United States Patent [19]

Bodine, Jr.

[11] Patent Number: 5,329,941
[45] Date of Patent: * Jul. 19, 1994

[54] ORTHOTIC HAND AND FOREARM SUPPORT DEVICE

[76] Inventor: Robert C. Bodine, Jr., 30 Dianthus, Rancho Santa Margarita, Calif. 92688

[*] Notice: The portion of the term of this patent subsequent to Oct. 29, 2008 has been disclaimed.

[21] Appl. No.: 780,856

[22] Filed: Oct. 18, 1991

Related U.S. Application Data

[63] Continuation-in-part of Ser. No. 452,627, Dec. 14, 1989, Pat. No. 5,060,638.

[51] Int. Cl.⁵ ............................................. A61F 5/10
[52] U.S. Cl. ................................... 128/845; 128/878; 297/466; 297/DIG. 4; 602/12; 602/21
[58] Field of Search ................... 602/6, 12, 20, 21, 36; 128/845, 846, 869, 878, 879; 5/621, 623, 630, 646, 647; 297/466, DIG. 4

[56] References Cited

U.S. PATENT DOCUMENTS

| | | |
|---|---|---|
| 2,693,794 | 11/1954 | Neville . |
| 3,287,064 | 11/1966 | Freeman . |
| 3,644,949 | 2/1972 | Diamond ............................. 5/630 |
| 3,678,926 | 7/1972 | Strittmatter ....................... 5/647 X |
| 3,746,332 | 7/1973 | Hakstian . |
| 3,903,878 | 9/1975 | Spann . |
| 4,235,472 | 11/1980 | Sparks et al. ..................... 5/646 X |
| 4,265,232 | 5/1981 | Stonich . |
| 4,270,235 | 6/1981 | Gutmann . |
| 4,549,537 | 10/1985 | Ender . |
| 4,566,449 | 1/1986 | Smith ............................... 128/845 |
| 4,576,351 | 3/1986 | Brink . |
| 4,896,660 | 1/1990 | Scott ................................. 602/20 |
| 5,035,015 | 7/1991 | Maietta ............................. 5/630 |
| 5,060,638 | 10/1991 | Bodine, Jr. ................... 128/845 X |

OTHER PUBLICATIONS

Photocopies of 4 pages from Fred Sammons, Inc. Catalog.
Photocopies of 3 pages from "Pictorial Reference Manual of Orthotics and Prosthetics", published by American Orthotics & Prosthetics Association.

Primary Examiner—Richard J. Apley
Assistant Examiner—Linda C. M. Dvorak

[57] ABSTRACT

A hand and forearm orthotic device for attachment to the forearm of chronically ill, elderly, handicapped, comatose or deliberated patients. The device comprises a block member, preferably formed of flexible foam or other soft material having a pair of support members releasably attached to the underside thereof. The block member incorporates a pair of retainer straps operative to hold a human forearm in a first position thereon. A hand support assembly is also connected to and/or incorporated in the block member so as to support the hand of the patient when the forearm is positioned on top of the block member. The hand support assembly may be adjustable so as to provide for varying degrees of rotation or dorsiflexion of the hand. A longitudinal groove formed by the support members and the underside of the block member may be used to facilitate placement of the block member on a wheelchair arm or other structure. The orthotic device further includes an optional axillary wedge member or abductor assembly attachable to the forearm support device to abduct the shoulder joint. The wedge member may be adjustable to accomplish varying degrees of abduction.

38 Claims, 5 Drawing Sheets

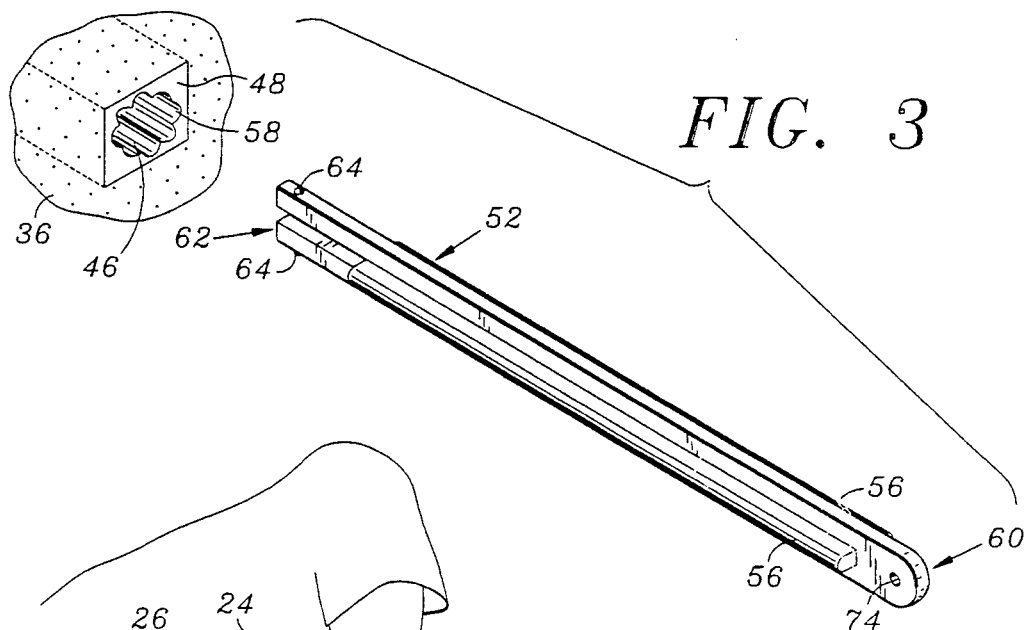
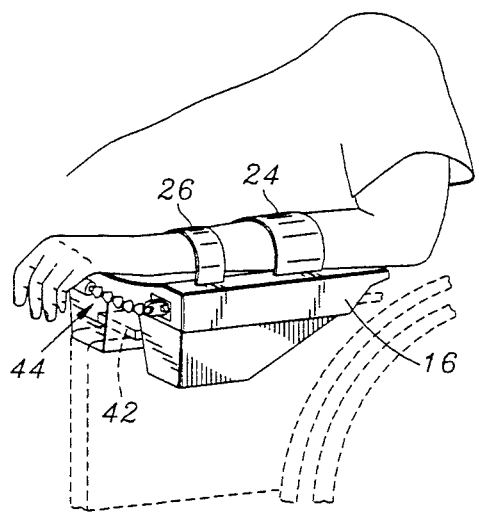
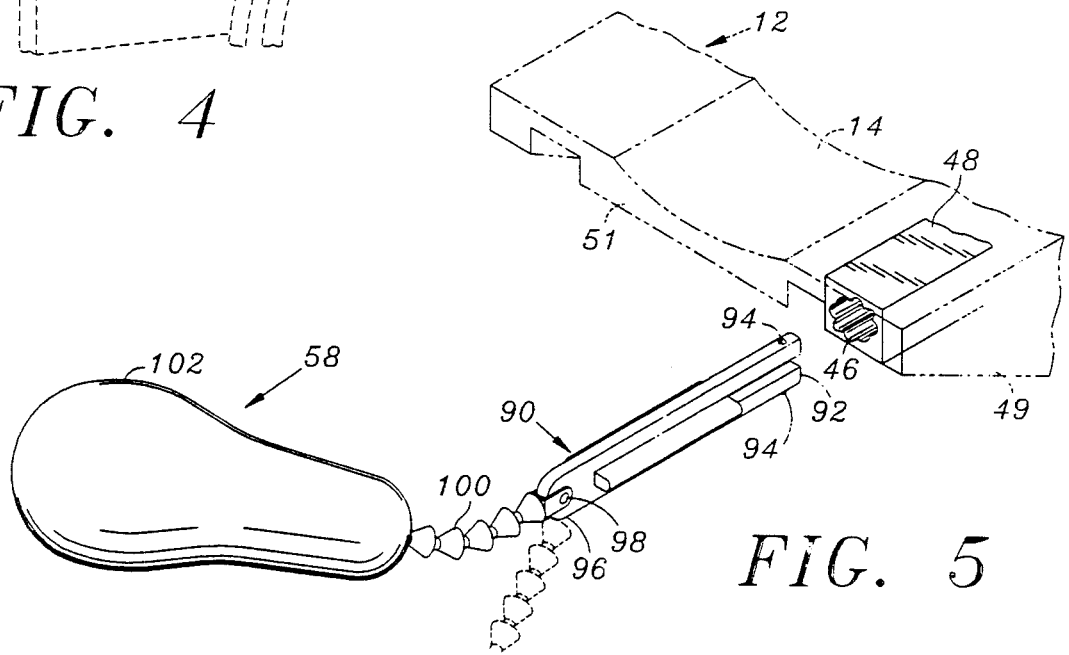

ORTHOTIC HAND AND FOREARM SUPPORT DEVICE

FIELD OF THE INVENTION

The present application is a continuation-in-part of application Ser. No. 07/452,627 filed Dec. 14, 1989, now U.S. Pat. No. 5,060,638 the disclosure of which is hereby incorporated by reference. The present invention pertains generally to medical equipment and more particularly to a device for restraining and shielding the forearm and hand and also for effecting orthosis of the entire pectoral limb including the hand, wrist, arm, elbow and shoulder of patients who are ill, handicapped, elderly, or comatose.

BACKGROUND OF THE INVENTION

Chronically ill, elderly, severely handicapped, and/or comatose patients sometimes require restraint and/or cushioning of the hands and forearms to prevent self-injury and/or to maintain a posture which will present or minimize the development of muscular atrophy, edema, decubitus, and/or acute pressure sores.

Severely debilitated patients often tend to assume a posture wherein their arms become folded or retracted against the anterior thorax and/or shoulders. If such posture is allowed to remain uncorrected for an extended period of time, the muscles of the arms and shoulders will begin to atrophy. Additionally, the constant positioning of the patient's hands adjacent the anterior thorax often results in repeated scratching (i.e. fingernail trauma) of the chest and neck area.

Additionally, in some patients who remain comatose or bedridden for extended periods of time, a condition known as "wrist drop" (syn. carpoptasis, drop hand) may result. Wrist drop is a muscular atrophy due to paralysis or non-use of the extensor muscles of the hand and fingers.

Also, in some patients edema of the hands and wrists may develop if their hands and arms are not maintained in an elevated posture. This problem of edema formation is especially prevalent in patients whose cardiac function is compromised (e.g. edematous changes which result from congestive heart failure).

Those who provide care to chronically ill, elderly, severely handicapped, or comatose patients often undertake to restrain or affix the patient's arms in positions which will help to retain normal muscle tone and prevent accidental trauma. Such restraint is typically accomplished through the use of straps or tape. For example, the forearms of an elderly patient may be loosely taped or bound to the arms of a wheelchair so as to prevent the arms from falling into the spokes of the wheelchair wheels and becoming injured thereby. Also, to prevent patients from scratching or injuring themselves, it is common practice to cushion the hands or to place a pillow on the patient's chest and to allow the patient's arms to retract against the pillow, thereby avoiding direct contact between the hands and the patient's body.

Although wheelchair "arm trays" and other orthotic appliances are available, such appliances are generally usable only in fixed locations (e.g., on the arm of a wheelchair) and do not generally attach to the patient's limb in a portable manner so as to permit the patient to move the limb about with the orthotic device remaining attached thereto.

Although these prior art methods and practices and devices may be somewhat helpful in preventing muscular atrophy, injury and/or edema, the common practice of taping or strapping the arms is known to be cumbersome and also tends to be somewhat imposing in appearance. Thus, there exists a need in the art for a simple device, attachable to the forearm, to effect restraint and shielding of the forearms/hands of a patient without the need for deployment of ties, cords, tapes, or the like. Additionally, it is desirable that such device be usable to accomplish orthosis of the entire pectoral limb, including the hand, wrist, arm, elbow, and shoulder.

In recognition of the aforementioned need, applicant developed the hand and forearm orthotic device disclosed in parent application Ser. No. 07/452,627 entitled "ORTHOTIC AND RESTRAINING DEVICE POSITIONABLE ON THE HAND AND FOREARM". This particular device generally comprises a block member having a strap member attached thereto to bind a forearm to the upper surface thereof. The block member has a generally wedge-shaped configuration such that when resting on a generally flat surface, the forearm is elevated such that the hand is higher than the remainder of the forearm. The device further includes a generally cylindrical hand grip adjustably attached to the block member via arcuate mounting members so as to permit varying degrees of dorsiflexion of the hand.

Though this particular device alleviates many of the shortcomings of the prior art, the device possesses certain deficiencies which detracts from its overall utility. One such deficiency is the inability of the device to permit varying degrees of rotation of the hand in addition to dorsiflexion. Further, due to the wedge-shaped configuration of the block member, the block member may not be used to maintain the forearm in a generally horizontal orientation unless such is affixed to a support member such as the armchair portion of a wheelchair. Additionally, the block member is not constructed so as to allow for the adjustment of the inclination angle of the patient's forearm. The present invention alleviates these and other deficiencies associated with the prior art, including the orthotic device disclosed in the parent application.

SUMMARY OF THE INVENTION

In accordance with a first embodiment of the present invention, there is provided a hand and forearm orthotic device generally comprising a block member having a front end, a rear end, a generally flat upper surface, and a generally flat underside. Releasably attached to the underside of the block member is a pair of support members, each having a front end, a rear end and a bottom surface. The orthotic device further comprises a retainer strap operative to hold a human forearm in a first position on the upper surface of the block member and a hand support assembly attached to and extending forward of the front end of the block member to engage the hand when the forearm is in the first position upon the upper surface. In the first embodiment, the block member and the support members are shaped such that when interconnected, the upper surface to bottom surface dimension at the front ends of the block member and the support members is greater than the upper surface to bottom surface dimension at the rear ends of such members. In this respect, when the bottom surfaces of the support members are positioned on a horizontally planar underlying surface, the forearm, when in the first position, will be inclined such that the wrist is higher than the elbow.

In the first embodiment, the support members are identically configured and have generally L-shaped configurations. The support members each define an inner sidewall and an outer sidewall, and are selectively attachable to the block member in a manner wherein the inner sidewalls of the support members and the underside of the block member form a generally rectangular notch which is sized and configured to receive the armrest of a wheelchair. In a second embodiment, the inner sidewalls are preferably slanted such that when the support members are positioned on either side of the armrest, the armrest will be frictionally retained therebetween.

The block member of the device further includes a pair of longitudinal channels formed therein which open through the front end of the block member. The hand support assembly comprises a pair of elongate members having proximal and distal ends, the proximal ends being slidably receivable into a respective one of the channels such that the elongate members are alternately extensible and retractable therein. Importantly, the channels and the elongate members are configured such that the elongate members are selectively, rotatably positionable within the channels. The hand support assembly further comprises a hand engaging element mounted to the distal ends of the elongate members which is sized, configured and positioned to engage and support the patient's hand forward of the front end of the block member when the forearm is in the first position. The hand engaging element preferably includes a pair of flexible extensions connected to the distal ends of the elongate members, and a generally cylindrical hand grip connected to and extending between the flexible extensions. Importantly, the flexible extensions are configured to selectively adjust the position of the handle grip relative the block member so as to affect varying degrees of dorsiflexion and/or rotation of the hand when the forearm is in the first position. In accordance with an alternative embodiment of the present invention, the hand support assembly may comprise a single elongate member having a single flexible extension attached to the distal end thereof, the handle grip being connected to and extending perpendicularly from the distal end of the flexible extension.

The orthotic device further includes a trough formed in the upper surface of the block member which is sized and configured to receive at least a portion of the forearm therein. The retainer strap preferably comprises first and second strap members connected to a pad which is releasably attachable to the block member in a manner substantially covering the upper surface thereof. When the device is used to elevate the forearm, the support members are attached to the underside of the block member in a manner wherein the portions of the inner sidewalls are in abutting contact. When the support members are oriented in this manner, a wrap member which is releasably attachable to the block member is used to maintain the support members in attachment to the underside of the block member.

The orthotic device of the present invention further includes at least one wedge member which is selectively insertable between the block member and the support members. The wedge member is operable to increase the inclination angle of the forearm when the bottom surfaces of the support members are positioned on a horizontally planar surface. Additionally, the orthotic device may include an axillary abductor member attached to and extending forward of the rear end of the block member which is selectively positionable between the shoulder and torso of the patient when the forearm is in the first position on the block member. The axillary abductor member preferably comprises an elongate member slidably receivable into one of the channels at the rear end of the block member. A flexible extension is connected to the distal end of the elongate member, and an abductor member such as a wedge-shaped pad is connected to the distal end of the flexible extension.

BRIEF DESCRIPTION OF THE DRAWINGS

These as well as other features of the present invention will become more apparent upon reference to the drawings wherein:

FIG. 3 is an exploded view illustrating the interface of a hand support assembly component to the block member of the orthotic device;

FIG. 4 is a perspective view illustrating the engagement of the orthotic device to the armrest portion of a wheelchair;

FIG. 5 is a perspective view illustrating an axillary abductor member engageable to the block member of the orthotic device;

DETAILED DESCRIPTION OF THE PREFERRED EMBODIMENT

Figure 1:
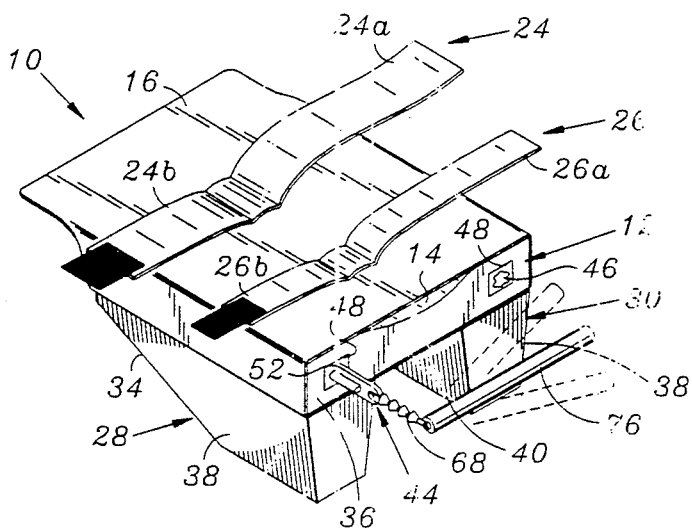
FIG. 1 is a perspective view of the orthotic device constructed in accordance with one embodiment of the present invention.
Figure 2:
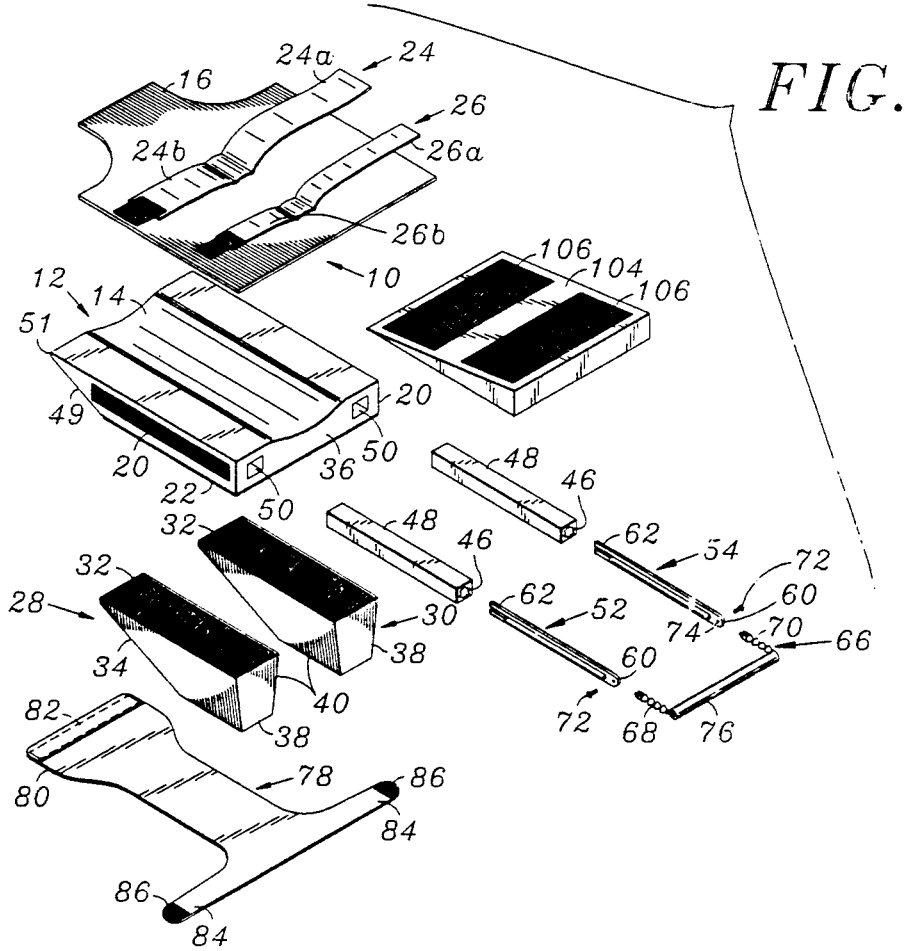
FIG. 2 is an exploded view of an orthotic device constructed in accordance with an alternative embodiment of the present invention.

Referring now to the drawings wherein the showings are for purposes of illustrating alternative embodiments of present invention only, and not for purposes of limiting the same, FIG. 2 is an exploded view of an orthotic device 10 constructed in accordance with a first embodiment of the present invention. As seen in FIGS. 1 and 2, orthotic device 10 generally comprises a block member 12. The block member 12 may be formed of any materials which will enable the block member 12 to achieve the uses, functions, and applications herein described. It is preferable that at least the outer surface of the block member 12 be formed of material which is sufficiently soft to avoid the likelihood of injury to the wearers body. At the same time, the block member 12 should exhibit sufficient internal structural integrity and rigidity to carry out the hereinafter described functions of the device of the present invention. Such combination of structural integrity and surface softness may be achieved by forming the core of the block of a rigid (e.g. solid plastic, metal) material and providing a soft outer covering (e.g. flexible/resilient plastic foam) formed on at least some of the outer surfaces of the rigid core. A slight trough 14 is formed in the upper surface of the block member 12 so as to permit the forearm of a human being to rest comfortably within such trough 14. The trough 14 may be molded into the overall configuration of the block member 12 or may be subsequently cut or machined away after the block member 12 has been preformed with a substantially flat upper surface.

Releasably attached to the block member 12 is a pad 16 which is preferably fabricated from a layer of polyurethane foam covered by nylon weave fabric. Pad 16 is sized and configured to cover the entire upper surface of the block member 12 and includes portions which extend over the opposed longitudinal sides of block member 12. To facilitate the releasable attachment of pad 16 thereto, disposed on the opposed longitudinal sides of block member 12 are strips of a hook and loop connector material 20 (e.g. Velcro) or any other suitable connector, which is operable to releasably join the pad 16 to the block member 12 in the manner shown in FIG. 1. A first retainer strap 24 and a second retainer strap 26 are attached to the pad 16 and are provided to hold the forearm of a patient firmly yet comfortably upon the pad 16 and within the trough 14 of the upper surface of the block member 12. First retainer strap 24 consists of first 24a and second 24b strap portions while second retainer strap 26 consists of first 26a and second 26b strap portions. The strap portions 24a and 24b and the strap portions 26a and 26b are joinable over the center portion of the upper surface of the block member 12 when used to secure the forearm thereto. The strap portions 24b and 26b further include hook and loop connector material on the ends thereof to releasably join strap portions 24a, 26a, respectively. Thus, when the forearm of the patient is placed on the upper surface of the block member 12, retainer straps 24 and 26 may be securely fastened over the top of the forearm thereby holding the forearm of the patient in position on the upper surface of the block member 12 in the manner shown in FIGS. 4 and 7.

Releasably attached to the underside of the block member 12 are a first support member 28 and a second support member 30. To facilitate the releasable attachment of each of the support members 28, 30 to the underside of the block member 12, disposed on the upper surface of each of the support members are Velcro strips 32 which are releasably engageable to a Velcro sheet 22 attached to the underside of the block member 12. Support members 28 and 30 are each formed to include a bottom surface having an inclined portion 34. In the preferred embodiment, each of the support members 28, 30 is generally L-shaped and includes a generally flat outer sidewall 38, a first inner sidewall 40 and a second inner sidewall 41. When the orthotic device 10 is to be interfaced to a structural member such as to an armrest 42 of a wheelchair, as shown in FIG. 4, the support members 28, 30 are attached to the block member 12 in a manner wherein the inner sidewalls 40, 41 thereof face one another. In this respect, the support members 28, 30 are attached to the underside of the block member 12 in a manner wherein the front ends thereof are generally co-planar with the front end 36 of the block member 12 and the outer sidewalls 38 are generally co-planar with a respective one of the opposed longitudinal sidewalls of the block member 12 as seen in FIG. 1. When positioned in this particular orientation, the inner sidewalls 40, 41 and the underside of the block member 12 form a generally rectangular notch sized and configured to receive the armrest 42. When the orthotic device 10 is positioned on the armrest 42 in the manner shown in FIG. 4, the top surface of the armrest 42 is abutted against the underside of the block member 12 thereby causing the upper surface of the block member 12 to be horizontally oriented. In the preferred embodiment, the support members 28, 30 are made of flexible plastic foam, though other materials may be utilized as an alternative. As will be recognized, the detachability of the support members 28, 30 from the block member 12 allows the orthotic device 10 to be retained upon the forearm of the patient even in those instances when it is not desired to maintain the forearm in an inclined orientation.

Referring now to FIGS. 1–3, the orthotic device 10 further comprises a hand support assembly 44 attached to and extending forward of the front end 36 of the block member 12 to engage the hand of a patient when the forearm is attached to the block member 12 via the retainer straps 24, 26. To facilitate the attachment of the hand support assembly 44 thereto, the block member 12 includes first and second identically configured longitudinal channels 46 opening through the front end 36 of block member 12 and oriented so as to be in substantially parallel relation. In the preferred embodiment, each of the channels 46 is formed within an elongate semi-rigid sleeve 48 which is received into a correspondingly shaped recess 50 formed within and extending longitudinally through the block member 12. The sleeves 48 are preferably formed from a material harder than the foam material used to fabricate the block member 12, e.g. a plastic material, and sized to extend from the front end 36 of the block member 12 to the lower edge of the angled portion 49 formed adjacent the rear end 51 thereof, as seen in FIG. 5. The hand support assembly 44 further comprises a first elongate member 52 and a second elongate member 54 which are identically configured and sized to be slidably receivable into and alternately extensible and retractable within a respective one of the channels 46 formed within the sleeves 48.

Referring now to FIG. 3, the elongate members 52, 54 and channels 46 are specifically configured such that the elongate members 52, 54 are selectively, rotatably positionable within a respective one of the channels 46. In this respect, each of the elongate members 52, 54 includes a pair of rib members 56 on opposed sides thereof, which are receivable into the arcuate serrations 58 defined within the channels 46. Additionally, the elongate members 52, 54 each include a proximal end 60 having a connector formed thereon as will be described below and a distal end 62 defining a pair of juxtaposed portions, each having a rounded stop projection 64 formed thereon. In interfacing the elongate members 52, 54 to the block member, the distal ends 62 thereof are slidably inserted into the channels 46. When the elongate members 52, 54 are extended from within the channels 46, the stop projections 64 formed on the distal ends 62 prevent the elongate members 52, 54 from being removed from the channels 46.

Mounted to the proximal ends 60 of the elongate members 52, 54 is a hand engaging element 66. Hand engaging element 66 generally comprises a first flexible extension 68 connected to the proximal end 60 of first elongate member 52 and a second flexible extension 70 attached to the proximal end 60 of second elongate member 54.

Figure 9:
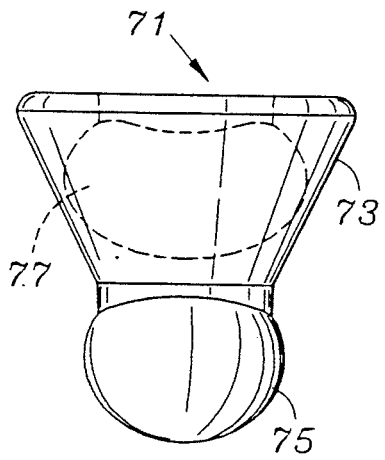
FIG. 9 is a front elevational view of a joint component used in the fabrication of flexible extensions of the orthotic device.
Figure 10:
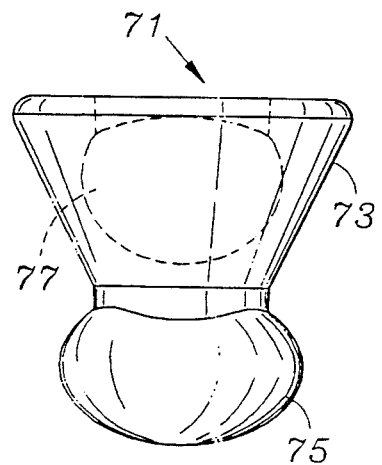
FIG. 10 is a side elevational view of the joint component shown in FIG. 9.
Figure 11:
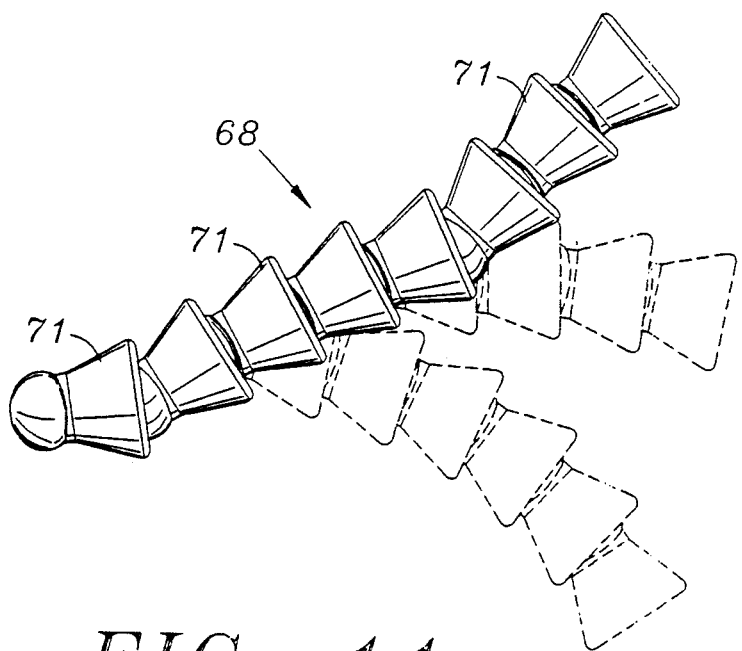
FIG. 11 is a side elevational view of a flexible extension fabricated from the joint components illustrated in FIGS. 9 and 10.

Referring now to FIGS. 9-11, flexible extensions 68, 70 are identically configured and preferably comprise a plurality of interconnected joint components 71, each of which have an overall length of approximately 0.750 inches. Joint components 71 each include a tapered portion 73 having a maximum outer diameter dimension of approximately 0.660 inches and a generally rounded male end 75 having a maximum outer diameter dimension of approximately 0.500 inches. Importantly, the male end 75 is fabricated so as to be oval, i.e. out of round, by approximately 0.030 of an inch. Disposed in the tapered portion 73 is a female recess 77 which is sized and configured to receive the male end 75 of a second joint component 71. The female recess 77 is sized such that there will be an interference fit of approximately 0.004-0.010 inches between the female recess 77 and the male end 75 of a second joint component when such is inserted thereinto. Importantly, the male end 75 and female recess 77 of each of the joint components 71 are formed so as to be opposed to one another by approximately 90 degrees. In this respect, because of the oval contour of the male end 75, such is prevented from fully rotating within a respective female recess 77. However, the oval contour of the male end 75 still allows for approximately 50 degrees of rotational movement of the male end 75 within the female recess 77. As such, due to the 90-degree offset between the male end 75 and female recess 77 of the interconnected joint components 71, the greater number of joint components 71 that are interconnected, the greater the amount of rotation that is obtainable, i.e. each additional unit provides another 50 degrees of rotation. Thus, if only two joint components 71 are interconnected, the amount of obtainable rotation of the flexible extensions 68, 70 would be minimal, i.e. only about 50 degrees. As each additional joint component 71 is added in the construction of the flexible extensions 68, 70, the rotational capacity is incrementally increased. Each of the joint components 71 are preferably injection molded from a compliant material such as polypropylene or polyethylene, though other materials may be utilized as an alternative.

Flexible extensions 68, 70 are preferably attached to members 52, 54 by the receipt of male connectors which are formed on the proximal ends 60 of members 52, 54 and identically configured to male ends 75 into the female recesses 71 of extensions 68, 70. As an alternative, fasteners such as pins which extend through respective ones of the extensions 68, 70 and apertures disposed in the proximal ends 60 of elongate members 52, 54 may be used to facilitate the attachment. Mounted to and extending between the distal ends of the flexible extensions 68, 70 is a hand grip 76 having a generally cylindrical configuration. Hand grip 76 is preferably formed to include recesses on the opposed ends thereof which are identically configured to the female recesses 77 and thus adapted to receive the male ends 75 of flexible extensions 68, 70. In the preferred embodiment, the flexible extensions 68, 70 are configured to allow the position of the hand grip 76 to be selectively adjusted relative the block member 12 so as to affect varying degrees of dorsiflexion of the hand of the patient when the forearm is secured to the block member 12. Additionally, the flexible extensions 68, 70 are operable to selectively adjust the position of the hand grip 76 so as to affect varying degrees of rotation of the hand of the patient relative the block member 12. As will be recognized, the position of the hand grip 76 relative the front end 36 of the block member 12 may also be adjusted inwardly or outwardly via the selective retraction or extension of the elongate members 52, 54 within the longitudinal channels 46. As such, the hand engaging element 66 may be positioned in accordance with the size of the patient's hand and wrist and retained in the desired position by the frictional engagement between the stop members 64 and channels 46.

As seen in FIG. 1, in accordance with a second embodiment of the invention the hand support assembly 44 may be fabricated so as to include only the first elongate member 52 as opposed to including the first and second elongate members 52, 54 shown in FIG. 2. In this alternative embodiment, the hand engaging element 66 comprises only the first flexible extension 68 which is connected to the proximal end 60 of the first elongate member 52 and the hand grip 76 which is connected to and extends perpendicularly from the distal end of the first flexible extension 68. As will be recognized, when the second elongate member 54 and second flexible extension 70 are eliminated from the hand support assembly 44 as shown in FIG. 1, a greater degree of rotation of the hand grip 76 is obtainable. As previously indicated, the hand support assembly 44 may be selectively adjusted so as to permit varying degrees of dorsiflexion and/or rotation of the patient's hand. In facilitating the dorsiflexion and/or rotation, it will be recognized that when only first elongate member 52 and first flexible extension 68 are utilized in fabricating hand engaging element 66, first elongate member 52 may be inserted into the channels 46 defined within either of the sleeves 48.

Figure 6:
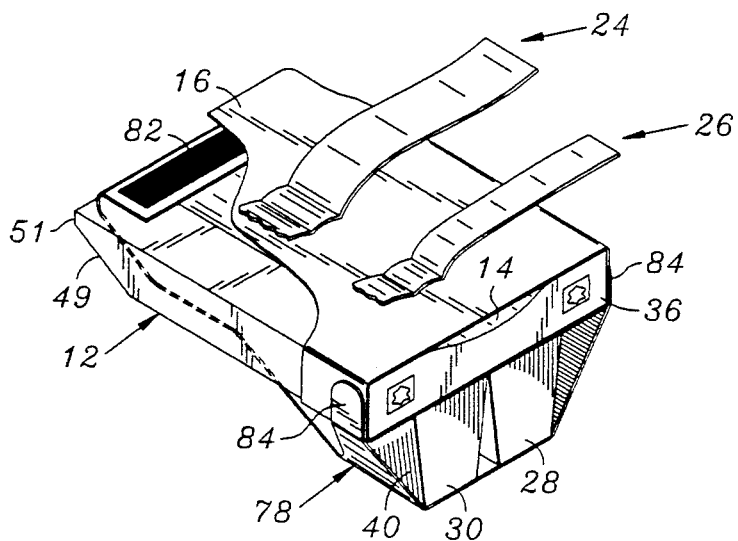
FIG. 6 is a perspective view illustrating an alternative method of attaching the support members to the block member of the orthotic device.
Figure 7:
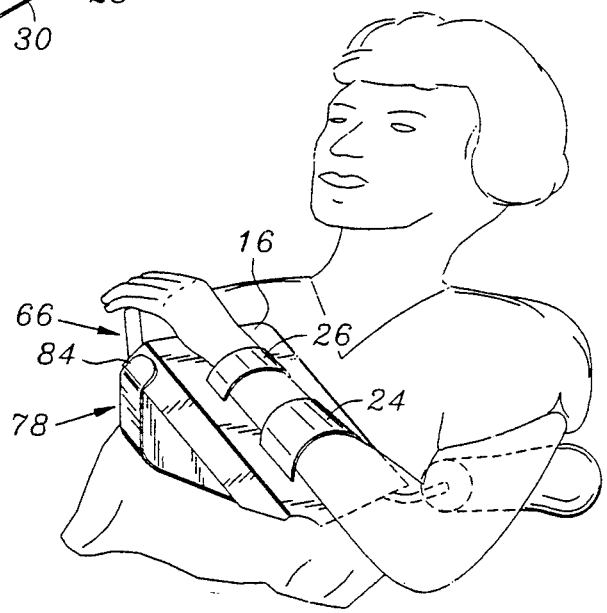
FIG. 7 is a perspective view illustrating the manner in which the orthotic device is used to elevate a patient's forearm when the support members are oriented in the manner shown in FIG. 6.

Referring now to FIG. 6, the inner sidewalls 40, 41 of the support members 28, 30 are fabricated so as to have a generally flat configuration. In this respect, when the orthotic device 10 is utilized to elevate the forearm of the patient in an angled orientation, the support members 28, 30 are preferably attached to the underside of the block member 12 below the trough 14 such that the first inner sidewalls 40 are in abutting contact. When positioned in this manner, the support members 28, 30 are retained in attachment to the underside of the block member 12 via a wrap member 78 having a generally T-shaped configuration. The wrap member 78 includes a rear portion 80 having a Velcro strip 82 attached thereto. The rear portion 80 is sized to extend over the rear end 51 of block member 12 in a manner wherein the Velcro strip 82 faces upwardly from the upper surface of the block member 12. As best seen in FIG. 6, the rear portion 80 of wrap member 78 is attached to the block member 12 by the engagement of the Velcro strip 82 to the pad 16. The wrap member 78 further includes a pair of lateral extensions 84 having Velcro patches 86 disposed on the distal ends thereof. The Velcro patches 86 are engaged to the pad 16 adjacent the front end 36 of the block member 12 to attach the front end of the wrap member 78 thereto. With the wrap member 78 being interfaced to the pad 16 and support members 28, 30 in the aforementioned manner, the orthotic device 10 is used to maintain the forearm of the patient in an elevated orientation as shown in FIG. 7. It will be recognized that support members 28, 30 may be utilized to maintain the forearm in an angled orientation without the utilization of the wrap member 78, though the wrap member 78 serves to provide an additional cushion between the support members 28, 30 and chest of the patient.

Referring now to FIGS. 5 and 7, the orthotic device 10 of the present invention may further include an abductor assembly, abductor member or axillary wedge assembly 88 attached to and extending forward of the rear end 51 of the block member 12. As seen in FIG. 7, the abductor member or axillary wedge assembly 88 is selectively positionable between the shoulder and torso of the patient when the forearm is secured to the orthotic device 10. In the preferred embodiment, the abductor member or axillary wedge assembly 88 generally comprises a third elongate member 90 having a configuration identical to, but substantially shorter than, the first and second elongate members 52, 54. Particularly, third elongate member 90 includes a distal end 92 consisting of a pair of juxtaposed portions having stop projections 94 formed thereon and a proximal end 96 having a connector formed thereon which is identically configured to the male end 75 of a joint component 71. Attached to the connector formed on proximal end 96 is a third flexible extension 100 having a configuration identical to first and second flexible extensions 68, 70. Connected to the distal end of the third flexible extension 100 is a wedge-shaped pad member 102. Abductor member or axillary wedge assembly 88 is interfaced to block member 12 via the slidable receipt of the distal end 92 of the third elongate member 90 into the rear end of either of the longitudinal channels 46 formed within sleeves 48. As will be recognized, the particular sleeve 48 into which the abductor member or axillary wedge assembly 88 is inserted will be dependent upon the arm of the patient to which the orthotic device 10 is secured. Though being alternately extensible and retractable within one of the channels 48, the distal end 92 of the third elongate member 90 is retained therewithin via the stop projections 94 formed thereon. Additionally, in constructing the abductor member or axillary wedge assembly 88, the proximal end of third flexible extension 100 may be rigidly attached to the rear end 51 of block member 12, thereby eliminating the use of third elongate member 90.

Figure 8:
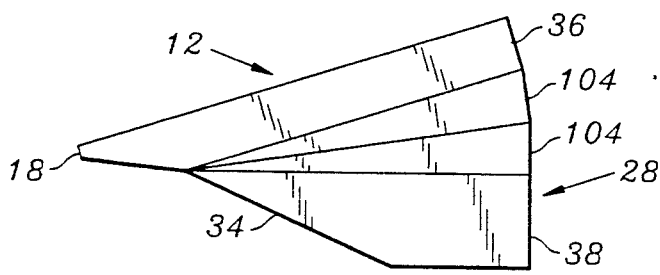
FIG. 8 is a side elevational view illustrating the insertion of a plurality of wedge members between the block member and support members of the orthotic device.

Referring now to FIGS. 2 and 8, when the orthotic device 10 is utilized to maintain the forearm of the patient in an angled orientation, the angle of inclination may be selectively increased beyond that which is obtainable by the interface of the support members 28, 30 to the block member 12 via the insertion of one or more wedge members 104 therebetween. Each of the wedge members 104 is preferably constructed from a foam rubber material and includes Velcro strips 106 attached to the upper and lower surfaces thereof. The Velcro strips 106 on the upper and lower surfaces of the wedge members 104 are engageable to the Velcro sheet 22 on the underside of the block member 12 and to the Velcro strips 32 disposed on the top surfaces of the support members 28, 30. As will be recognized, the greater the number of wedge members 104 inserted between the support members 28, 30 and block member 12, the greater the inclination angle of the patient's forearm.

Figure 12:
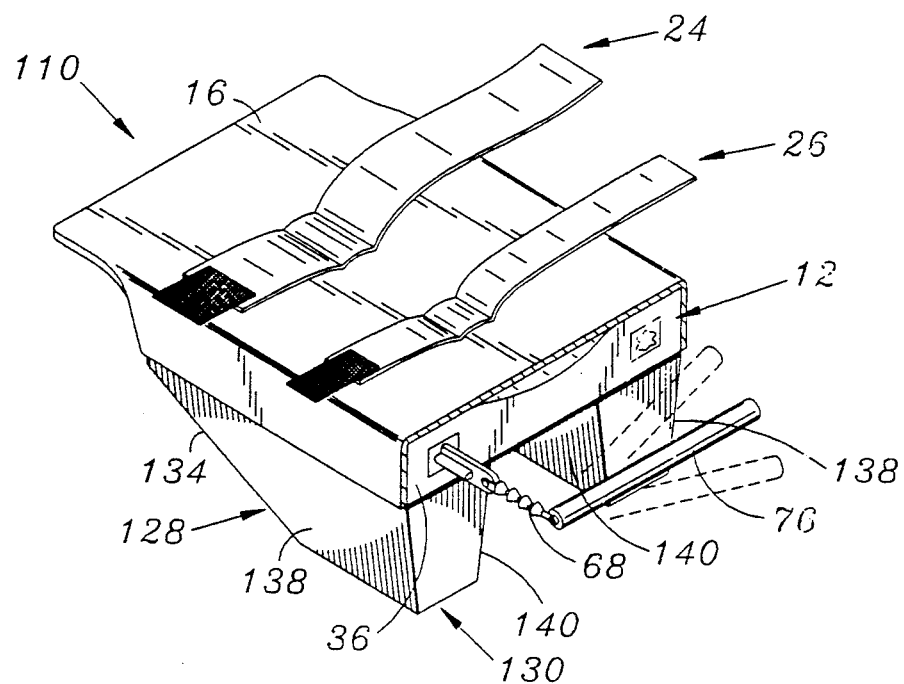
FIG. 12 is a perspective view of the orthotic device including support members constructed in accordance with the second embodiment of the present invention.
Figure 13:
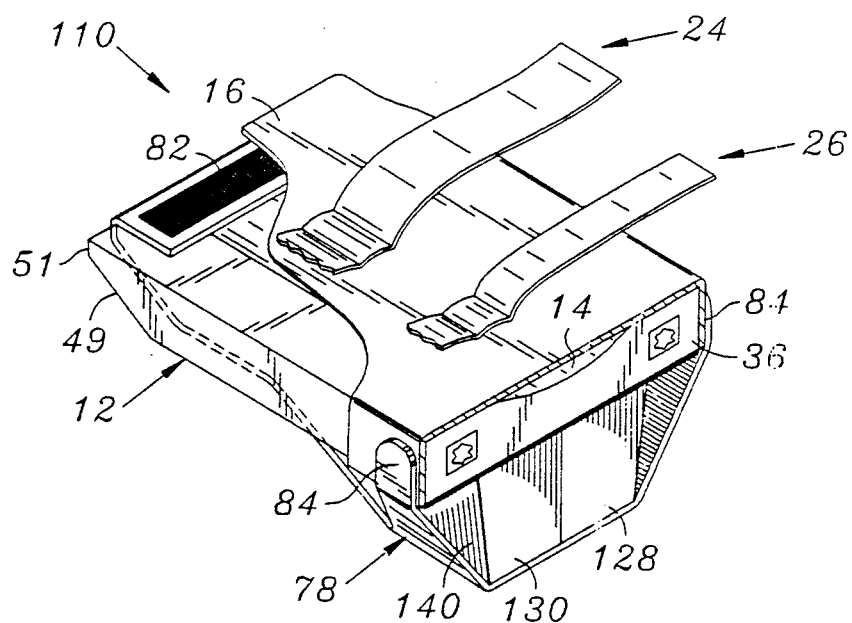
FIG. 13 is a perspective view illustrating an alternative method of attaching the support member constructed in accordance with the second embodiment to the block member of the orthotic device.

Referring now to FIGS. 12 and 13, disclosed is an orthotic device 110 constructed in accordance with an alternative embodiment and incorporating support members 128, 130, each of which include a bottom surface having an inclined portion 134, a generally flat outer sidewall 138 and a slanted inner sidewall 140. When the orthotic device incorporating the support members 128, 130 is interfaced to a structural member such as the armrest 42 of a wheelchair, the support members 128, 130 are attached to the block member 12 in a manner wherein the slanted inner sidewalls 140 thereof face one another. In this respect, the support members 128, 130 are attached to the underside of the block member 12 in a manner wherein the front ends thereof are generally co-planar with the front end 36 of the block member 12 and the outer sidewalls 138 are generally co-planar with respect to one of the opposed longitudinal sidewalls of the block member 12. When positioned in this particular orientation, the inner sidewalls 140 and the underside of the block member 12 form a generally rectangular notch sized and configured to receive the armrest 42. As will be recognized, due to the slanted configuration of the inner sidewalls 40, the armrest 42 will be frictionally retained between the support members 128, 130 when disposed therebetween.

As previously indicated, the outer sidewalls 138 of the support members 128, 130 are fabricated so as to have a generally flat configuration. In this respect, when the orthotic device 110 is utilized to elevate the forearm of the patient in an angled orientation, the support members 128, 130 are preferably attached to the underside of the block member 12 below trough 14 such that the outer sidewalls 138 are in abutting contact. When positioned in this manner, the support members 128, 130 are retained and attachment to the underside of the block member 12 via the wrap member 78, though it will be recognized that the support members 128, 130 may be utilized to maintain the forearm in an angled orientation without the utilization of the wrap member 78.

Additional modifications and improvements of the present invention may also be apparent to those skilled in the art. Thus, the particular combination of parts described and illustrated herein is intended to represent only one embodiment of the invention, and is not intended to serve as limitations of alternative devices within the spirit and scope of the invention.

What is claimed is:

1. A hand and forearm orthotic device comprising:
   a block member having a front end, a rear end, a generally flat upper surface, and a generally flat underside;
   at least one support member releasably attached to said underside of said block member, said support member having a front end, a rear end and a bottom surface;
   a retainer strap operative to hold a human forearm in a first position on the upper surface of said block member; and
   a hand support member attached to and extending forward of the front end of said block member to engage the hand when said forearm is in said first position;
   said block member and said at least one support member being shaped such that when interconnected, the upper surface to bottom surface dimension at the front end of said block member and said support member is greater than the upper surface to bottom surface dimension at the rear end of said block member and said support member such that when the bottom surface of said support member is positioned on a horizontally planar underlying surface, the forearm in said first position on the upper surface of the block member will be inclined such that the wrist is higher than the elbow.

2. The orthotic device of claim 1 wherein said at least one support member comprises a pair of support members, each of said support members being releasably attachable to said underside of the block member.

3. The orthotic device of claim 2 wherein each of said support members define an inner sidewall and an outer sidewall, said support members being selectively attachable to said underside in a manner wherein said inner sidewalls and said underside form a generally rectangular notch sized and configured to receive an armrest of a wheelchair.

4. The orthotic device of claim 3 wherein each of said inner sidewalls is slanted such that when positioned on either side of the armrest, the armrest will be frictionally retained therebetween.

5. The orthotic device of claim 4 wherein each of said outer sidewalls is generally flat, said support members being selectively attachable to said underside in a manner wherein said outer sidewalls are in abutting contact.

6. The orthotic device of claim 2 wherein each of said support members defines first and second inner sidewalls and an outer sidewall, said support members being selectively attachable to said underside in a manner wherein said first and second inner sidewalls and said underside form a generally rectangular notch sized and configured to receive an armrest of a wheelchair.

7. The orthotic device of claim 6 wherein said first and second inner sidewalls are generally flat, said support members being selectively attachable to said underside in a manner wherein said first inner sidewalls are in abutting contact.

8. The orthotic device of claim 7 further comprising a wrap member releasably attachable to said block member, said wrap member being sized and configured to extend about and maintain said support members in attachment to said underside when said outer sidewalls are in abutting contact.

9. The orthotic device of claim 2 further comprising at least one wedge member selectively insertable between said block member and said support members, said wedge member being operable to increase the inclination angle of the forearm when the bottom surface of the support member is positioned on the horizontally planar surface.

10. The orthotic device of claim 2 wherein each of said support members are made of flexible plastic foam.

11. The orthotic device of claim 1 wherein said hand support member is movably mounted to said block member and includes means for selectively adjusting the position of the hand support member relative said block member so as to affect varying degrees of rotation of the hand when said forearm is in said first position.

12. The orthotic device of claim 1 wherein at least one longitudinal channel is formed within the block member, said longitudinal channel opening through said front end of said block member and further wherein said hand support comprises:

at least one elongate member having a proximal end and a distal end, the proximal end being slidably receivable into said channel such that said elongate member is alternately extensible and retractable into said channel, said channel and said elongate member being configured such that said elongate member is selectively, rotatably positionable within said channel; and a hand engaging element mounted to the distal end of the elongate member, said hand engaging element being sized, configured and positioned to engage and support the patient's hand forward of the front end of said block member when the forearm is in said first position.

13. The orthotic device of claim 12 wherein said hand engaging element comprises:

a flexible extension connected to the distal end of said elongate member; and a generally cylindrical hand grip connected to and extending perpendicularly from said flexible extension.

14. The orthotic device of claim 13 wherein said flexible extension is configured to selectively adjust the position of said hand grip relative said block member so as to affect varying degrees of dorsiflexion of the hand when said forearm is in said first position.

15. The orthotic device of claim 14 wherein said flexible extension is configured to selectively adjust the position of said hand grip relative said block member so as to affect varying degrees of rotation of the hand when said forearm is in said first position.

16. The orthotic device of claim 15 wherein said at least one channel is formed from a semi-rigid sleeve longitudinally disposed within said block member.

17. The orthotic device of claim 16 wherein said at least one longitudinal channel comprises a pair of longitudinal channels disposed within said block member in substantially parallel relation and said at least one elongate member comprises a pair of elongate member axially received into said channels, said hand engaging element being mounted to and extending between the distal ends of said elongate members.

18. The orthotic device of claim 1 wherein said hand support member includes means for selectively adjusting the position of the hand support member relative said block member so as to affect varying degrees of rotation and dorsiflexion of the hand when said forearm is in said first position.

19. The orthotic device of claim 18 wherein said hand support member comprises:

at least one flexible extension having a proximal end and a distal end, the proximal end being connected to and extending forward of the front end of said block member; and a hand engaging element mounted to the distal end of the flexible extension, said hand engaging element being sized, configured and positioned to engage and support the patient's hand forward of the front end of said block member when the forearm is in said first position;

said flexible extension being configured to selectively adjust the position of the hand engaging element relative the block member so as to affect varying degrees of rotation and dorsiflexion of the hand when the forearm is in said first position.

20. The orthotic device of claim 19 wherein said at least one flexible extension comprises a pair of flexible extensions connected to the front end of the block member in substantially parallel relation, said hand engaging element being mounted to and extending between the distal ends of said flexible extensions.

21. The orthotic device of claim 19 wherein said flexible extension comprises a plurality of interconnected joint components, each of said joint components having a male end of generally rounded, oval contour and a female recess disposed therein sized and configured to receive and frictionally retain the male end of a second joint component.

22. The orthotic device of claim 21 wherein the receipt of said male end into said female recess is adapted to provide approximately 50 degree of rotational movement between the interconnected joint members.

23. The orthotic device of claim 1 wherein a trough is formed in the upper surface of said block member, said trough being sized and configured to receive at least a portion of the forearm therein.

24. The orthotic device of claim 1 wherein said retainer strap comprises first and second strap members rigidly secured to a pad, said pad being releasably attachable to said block member in a manner substantially covering said upper surface.

25. The orthotic device of claim 1 further comprising a longitudinal groove formed in the bottom surface of said support member, said longitudinal groove being sized and configured to receive the armrest of a wheelchair therein such that said block member will rest stably on said wheelchair arm.

26. The orthotic device of claim 25 wherein said groove comprises a generally rectangular notch having first and second sidewalls and an upper surface.

27. The orthotic device of claim 26 wherein said first and second sidewalls are slanted such that when positioned on either side of the armrest of the wheelchair, the armrest will be frictionally retained therebetween.

28. The orthotic device of claim 1 further comprising at least one wedge member selectively insertable between said block member and said support member, said wedge member being operable to increase the incline of the forearm when the bottom surface of the support member is positioned on the horizontally planar surface.

29. The orthotic device of claim 1 further comprising an axillary wedge assembly attached to and extending forward of the rear end of the block member, said wedge assembly being selectively positionable between the shoulder and torso when the forearm is in the first position.

30. The orthotic device of claim 29 wherein said axillary wedge assembly comprises:
  a flexible extension having a proximal end and a distal end, said proximal end being rigidly connected to the rear end of the block member; and
  a wedge-shaped pad member connected to the distal end of the flexible extension.

31. The orthotic device of claim 1 wherein said block member is made of flexible plastic foam.

32. The orthotic device of claim 1 wherein at least a portion of said block members is made of plastic foam.

33. The orthotic device of claim 1 wherein said block member is made of substantially closed cell polyethylene foam.

34. The orthotic device of claim 1 wherein said block member comprises a generally rigid core having a soft outer cover disposed thereon.

35. The orthotic device of claim 1 wherein said block member comprises a rigid plastic core with a flexible foam outer cover disposed thereon.

36. The orthotic device of claim 1 wherein said support member is made of flexible plastic foam.

37. A hand and forearm orthotic device comprising:
  a block member having a front end, a rear end, a generally flat upper surface, and a generally flat underside;
  a retainer strap operative to hold a human forearm in a first position on the upper surface of said block member;
  a hand support member attached to and extending forward of the front end of said block member to engage the hand when said forearm is in said first position; and
  an axillary wedge assembly attached to and extending forward of the rear end of the block member, said axillary wedge assembly being selectively positionable between the shoulder and torso when the forearm is in the first position.

38. The orthotic device of claim 37 wherein said axillary wedge assembly comprises:
  a flexible extension having a proximal end and a distal end, said proximal end being rigidly connected to said rear end of the block member; and
  a wedge-shaped pad member connected to the distal end of the flexible extension.

* * * * *